(12) United States Patent
Strömberg et al.

(10) Patent No.: US 6,899,136 B1
(45) Date of Patent: May 31, 2005

(54) VALVE ARRANGEMENT

(75) Inventors: Stefan Strömberg, Sigtuna (SE); Nils Eriksson, Enskede (SE)

(73) Assignee: Aneo AB, Marsta (SE)

( * ) Notice: Subject to any disclaimer, the term of this patent is extended or adjusted under 35 U.S.C. 154(b) by 0 days.

(21) Appl. No.: 09/937,379

(22) PCT Filed: Mar. 23, 2000

(86) PCT No.: PCT/SE00/00576
§ 371 (c)(1),
(2), (4) Date: Sep. 24, 2001

(87) PCT Pub. No.: WO00/56386
PCT Pub. Date: Sep. 28, 2000

(30) Foreign Application Priority Data

Mar. 24, 1999 (SE) ............................................. 9901068

(51) Int. Cl.[7] ............................................. F16K 11/07
(52) U.S. Cl. ............................. 137/625.5; 137/625.42; 137/625.4
(58) Field of Search ....................... 137/625.18, 625.42, 137/625.5, 625.4

(56) References Cited

U.S. PATENT DOCUMENTS

| | | | | |
|---|---|---|---|---|
| 1,490,884 A | * | 4/1924 | Spreen | 137/625.5 |
| 2,046,474 A | * | 7/1936 | Maggenti | 251/216 |
| 3,194,264 A | * | 7/1965 | Greco | 137/556 |
| 3,424,260 A | * | 1/1969 | Stone et al. | 137/625.5 |
| 3,487,435 A | * | 12/1969 | Sheardown | 137/625.18 |
| 3,739,799 A | | 6/1973 | Bickford et al. | |
| 4,250,920 A | * | 2/1981 | Traylor | 137/625.29 |
| 4,711,270 A | * | 12/1987 | Fornasari | 137/625.5 |
| RE33,246 E | * | 7/1990 | Barree | 137/625.5 |
| 5,067,521 A | * | 11/1991 | Jenks et al. | 137/625.5 |

* cited by examiner

*Primary Examiner*—John Fox
(74) *Attorney, Agent, or Firm*—Banner & Witcoff, Ltd.

(57) ABSTRACT

The present invention relates to a mixing valve that can be included in pulmonary respiration equipment and with which oxygen (2) and air (3) can be mixed in adapted proportions. The mixing valve (1) comprises a valve housing (40) that has an internal cavity (46), which forms two mutually opposing valve seats (10d, 20d). The cavity (46) encloses an element (30) on which two valve bodies (10c, 20c) are formed. The cavity wall and the element have respective screw threads (46c' and 30c') which enable two valve means (10, 20) to be actuated so as to open one of said valve means and close the other to passage of media therethrough. The mixing valve is of simple construction and precise in operation and can be constructed with small outer dimensions.

20 Claims, 5 Drawing Sheets

VALVE ARRANGEMENT

This is a U.S. National Phase Application Under 35 USC 371 and applicant herewith claims the benefit of priority of PCT/SE00/00576 filed Mar. 23, 2000, which was published Under PCT Article 21(2) in English and Application No. 9901068-8 filed in Sweden on Mar. 24, 1999.

FIELD OF INVENTION

The present invention relates generally to a valve arrangement and more particularly to a valve arrangement, which is adapted to enable at least two media to be mixed in mutually different proportions.

To this end, the invention is based on a known valve arrangement which has a housing that includes a first inlet and first valve means for a first medium, and a second inlet and second valve means for a second medium.

The valve housing of the valve arrangement includes an outlet for respective media or an outlet for media mixed in the valve housing.

More specifically, the inventive valve arrangement is based on controlling movement of the valve body of a first valve means away from and towards a first valve seat, and the movement of the valve body of a second valve means away from and towards a second valve seat, in a manner such that when the flow of the first medium through the first valve means increases there will be a corresponding reduction in the flow of the second medium through the second valve means, and vice versa.

Valve arrangements of the afore-described kind are used for producing an air-oxygen gas-mixture in a pulmonary respirator or lung ventilator.

Valve arrangements of this kind can also be used beneficially with anaesthetic apparatus, where it is necessary to be able to adjust the mixture of oxygen gas and anaesthetic gas, such as nitrous oxide.

DESCRIPTION OF THE BACKGROUND ART

Several different types of valve arrangements of the aforesaid kind are known to the art and used for various purposes.

For instance, U.S. Patent Publication 3,739,799 illustrates and describes a control system for mixing two gases and for use with anaesthetic apparatus. The control system includes a mixing control valve which is adapted to be able to vary continuously the relative proportions between two gaseous components without needing to alter the total rate of flow through the valve to this end.

Also shown is a control unit for varying the total rate of flow of these components without needing to alter the relative proportion therebetween.

More particularly, there is disclosed in this prior publication a valve arrangement which is adapted to mix at least two media and which includes a first inlet and a first valve means for a first medium, and a second inlet and a second valve means for a second medium, and an outlet for respective media or an outlet for a media mixture.

According to this publication, movement of the valve body of a first valve means away from and towards a first valve seat, and movement of the valve body of a second valve means away from and towards a second valve seat are mutually controlled so that an increase in the flow of the first medium through the first valve means will result in a corresponding reduction in the flow of the second medium through the second valve means, and vice versa.

It is also disclosed that the valve seats of respective valve means are positioned in a respective valve housings, whereas the first and the second valve bodies are formed in the end parts of a rod-like element that includes a screw thread which co-acts with a corresponding screw thread on a first valve housing such as to enable the rod-like element to be displaced axially backwards and forwards in response to the direction in which said element is rotated.

In the case of this known arrangement, a wheel protrudes partially through a slot provided in an operating panel and is turned from outside said panel.

A valve arrangement in which rotation of a wheel causes the valve body of a first valve means to move to a closed position and the valve body of a second valve means to move to an open position through the medium of a gear-wheel arrangement is known from Swedish Patent Specification 330 749.

The German Patent Publication DE-A1-33 26 696 also discloses a valve arrangement in which two gases are mixed during a pressure difference balancing means and where the concentration of the mixture will be constant independently of pressure differences in the two gases.

This is caused by having a valve part attached to each of two diaphragms or membranes (7,8) and having valve seats (9,10) arranged between said membranes.

Each membrane is also supported by a spring arrangement (19,20) and the force caused by each of said spring arrangements is adjustable by a knob (21), the turning of which causes a higher or a smaller force.

This construction also includes two pressure chambers (15,16) one for each gas to be mixed. These pressure chambers are arranged between said membranes.

SUMMARY OF THE PRESENT INVENTION

Technical Problems

When taking into consideration the technical deliberations that a person skilled in this particular art must make in order to provide a solution to one or more technical problems that he/she encounters, it will be seen that on the one hand it is necessary initially to realise the measures and/or the sequence of measures that must be undertaken to this end, and on the other hand to realise which means is/are required in solving one or more of these problems. On this basis, it will be evident that the technical problems listed below are highly relevant to the development of the present invention.

When considering the present state of the art, as described above, it will be evident that a technical problem resides in providing with the aid of simple means a valve arrangement that is able to mix at least two media, particularly gaseous media, and that will function easily and has a simple construction which requires only a few readily produced components and which is very precise with respect to chosen mixing ratios.

It is also considered as a technical problem to take such steps that the complete valve arrangement can be dimensionally restricted to a small size.

It will also be seen that a technical problem is one of providing conditions with the aid of simple means that allow a first valve seat and a second valve seat to be formed in a readily produced cavity in a readily produced valve housing that comprises at least two parts, where the parts of said valve housing can be readily connected together with the aid of known fasteners, such as screw joints or co-acting threaded parts.

It will also be seen that a technical problem resides in providing a valve housing with an associated cavity from two identical or essentially identical end-related parts, each having a respective valve seat, and an intermediate, simple sleeve-like part, therewith enabling a valve arrangement to be constructed solely with the aid of an elongate rod-like element that has two readily produced end-orientated valve bodies.

Another technical problem will be seen to reside in the provision of conditions which enable the inner cavity of said valve housing to be formed with a threaded central part or a threaded end part and a rod-like element carrying said valve bodies to be provided with an external thread corresponding to the first-mentioned thread, so that an end part adapted for rotation of said element can be arranged to extend outside said valve housing in the form of a shaft, in one embodiment having a threaded section.

It will also be seen that a technical problem resides in realising the significance of and the advantages afforded by allowing the first and the second valve seats in the valve housing to be conical in shape (truncated), with the widest parts of the cones facing towards each other; and to give the first and second valve bodies a complementary conical shape, with the widest parts of the cones connecting with an intermediate externally threaded part of said element or just a small part.

It will also be seen that a technical problem is one of realising the significance of and the advantages associated with a valve arrangement adapted for the aforesaid application when said threads are given a pitch which will enable one of said valve bodies to be brought from a fully open position to a fully closed position in respect of its associated valve seat, and vice versa, by turning said element through 1–6 revolutions, such as just 2–4 revolutions.

It will also be seen that a technical problem resides in realising the significance of and the advantages afforded by providing a seal between said element and the inner wall of the cavity adjacent a threaded part, where the seal may conveniently comprise a sealing ring placed in a circular groove in the peripheral surface of said element or said cavity such as to prevent mixing of media in the valve housing and therewith enable the flow and/or volume of respective media to be measured.

It will also be seen that a technical problem resides in the provision of a seal between an end-related part of said element and the end-related part of said cavity with the aid of simple means, such as to prevent leaking of the first medium in the first valve means to the surrounding space.

The valve housing, which is at least in two parts, can be attached to an operating panel, with the rotatable shaft-like part extending beyond an exposable surface of the operating panel through an aperture or hole formed therein.

In this regard, a technical problem resides in providing with the aid of simple means a seal between the shaft-like part and the operating panel, or also between the valve housing and the operating panel.

In respect of a valve arrangement that includes two inlets and an outlet in the valve housing, another technical problem resides in providing conditions for and realising the advantages associated with providing the element with one or more axially orientated slots which extend between the valve bodies and open into a groove in said intermediate part, and for providing the valve housing with an outlet connecting with said groove.

In the case of a valve arrangement that includes two inlets and an outlet and intended for the aforesaid application, a technical problem resides in realising the significance of and the advantages afforded by providing the valve housing with one or more axially orientated slots that extend between the valve seats and a groove in the intermediate part, and by providing the valve housing with an outlet that connects with said groove.

In the case of this latter application, a technical problem resides in providing conditions with the aid of simple means which will allow the valve housing to be provided with an axially orientated slot that extends between mutually opposing valve seats, and with an outlet connecting with said slot so as to increase the enclosure angle of the thread within the valve housing and to permit a full enclosure angle of 360 degrees with respect to the thread on the rod-like element.

Another technical problem is one of realising the significance of providing the rod-like element with an externally threaded intermediate sleeve or the like offering the same function, and to permit said sleeve to be displaced axially in relation to said valve bodies.

Another technical problem is one of realising the significance of allowing the valve bodies to be fixed in relation to each other via a rod, and to provide between the rod and the sleeve means for preventing relative rotation therebetween and/or for making such rotation difficult.

In this respect, a technical problem is one of realising the significance of and the advantages afforded by allowing said means to have a three-edged or four-edged cross-sectional shape or some corresponding cross-sectional shape, or a cross-sectional shape that deviates slightly from a circular line, and by providing said sleeve with a centre bore whose cross-section conforms to the cross-section of said rod, or by implementing said means with the aid of a circular cross-section and keyway and a key for insertion into said keyway.

Another technical problem is one of realising the significance of and the advantages afforded by allowing the valve bodies to be fixed in relation to each other via a rod, and to provide between the rod and the sleeve means for making axial displacement difficult to achieve.

In this regard, a technical problem resides in realising the significance of and the advantages afforded by allowing this latter means to have the form of a spring unit, said spring unit conveniently comprising a compression spring that can be placed around or adjacent said rod, wherewith the spring is adapted to urge the sleeve in a direction away from the first valve means and into abutment with a support surface adjacent said second valve means.

With regard to a valve arrangement of the kind described in the introduction, it will also be seen that a technical problem resides in providing a rapid valve function which will allow an original intermediate mixture setting to be changed quickly to a setting that corresponds to 100% of the first medium and 0% of the second medium, by axially moving the rod-like element so as to seal-off the second valve means and to fully open the first valve means or vice versa.

It is also seen as a technical problem to arrange three separate parts around a means exposing the valve bodies arranged adjacent each other and hereby form a complete valve arrangement by the use of simple screws.

Solution

The invention is based on a known valve arrangement adapted for mixing together at least two media, wherein the valve arrangement includes an inlet and a valve means for a first medium, and an inlet and a valve means for a second medium, and an outlet for respective media or an outlet for a media mixture, wherein movement of the valve body of the first valve means away from and towards a first valve seat and movement of the valve body of the second valve means for movement away from and towards a second valve seat are mutually controlled so that an increase in the flow of the first medium through the first valve means will result in a reduction in the flow of the second medium through the second valve means, and vice versa, wherein the first and the second valve bodies have the form of a rod-like element.

With the intention of solving one or more of the aforesaid technical problems, it is proposed, in accordance with the present invention, that the first valve seat and the second valve seat of such a valve arrangement shall be formed in one and the same valve housing, whereby said housing comprises at least two parts, and that the internal cavity of said valve housing will include a central threaded part or an end-related threaded part, and that the rod-like element is provided with an external thread corresponding to the thread of said threaded housing part, and that one end of said element is caused to extend outside said valve housing for rotation of said element.

In accordance with proposed embodiments that lie within the scope of the inventive concept, it is proposed that the first and second valve seats are conical in shape (truncated) with the widest parts of the cones facing towards each other, and that the first and second valve bodies are conical in shape (truncated) with the widest parts of the cones connecting with the intermediate externally part of said element.

It is also proposed that the threads will have a pitch which will enable the valve bodies to be brought from a fully open position to a fully closed position in relation to their respective valve seats, by turning said element through 1–6 revolutions, such as 2–4, revolutions.

It is also proposed that a seal is provided adjacent the threaded intermediate part and that said seal will conveniently comprise a sealing ring placed in a circular groove in the peripheral surface of said element and/or in the housing cavity.

It is also proposed in accordance with the invention that the valve housing can be attached firmly to an operating panel with the rotatable end of said element extending through and beyond the operating panel.

A seal may be provided between the rod-like element and the valve housing, adjacent one end-part of said housing. The seal may be disposed between the end-part of said element and the valve housing such as to seal-off said first medium from passage to the surrounding space.

A seal may be disposed between the operating panel and the valve housing and/or between the operating panel and the rotatable end of said element and may have the form of a sealing ring placed in a circular groove, or may consist of foil.

In the case of a valve arrangement that includes two inlets and one outlet, it is proposed in accordance with the invention that the rod-like element is provided with one or more axially orientated slots that extend between the valve bodies and open into a groove in the intermediate part, and that the valve housing is provided with an outlet that connects with said groove.

In an alternative embodiment, it is proposed in accordance with the invention that the valve housing is provided with one or more axially orientated slots that extend between the valve seats and open into a groove in the intermediate part of the valve housing and/or into a groove in the intermediate part of the rod-like element, and that the valve housing is provided with an outlet positioned in connection with said groove.

In another alternative embodiment, the valve housing is provided with at least one axially orientated slot, which extends between the valve seats and with which the outlet connects.

It is also proposed that the rod-like element can include an externally threaded intermediate sleeve, which can be moved axially in relation to said valve bodies.

The valve bodies may be fixed in relation to each other via a rod, and means for preventing relative rotation of the rod and sleeve and/or making such rotation difficult is provided between said rod and said sleeve.

Such means may be obtained by giving the rod a triangular or square cross-section or some corresponding irregular cross-section, while providing the sleeve with a centre bore whose cross-sectional shape conforms to the cross-sectional shape of said rod.

For instance, said means may be obtained with a rod of circular cross-section and a centre hole in said sleeve of corresponding circular cross-section together with a keyway in both the rod and the sleeve and a key which co-acts with said keyway.

Alternatively, the valve bodies may be fixed in relation to one another through the medium of a rod with means for impeding axial displacement between the rod and the sleeve. Said means may have the form of a spring unit.

The spring unit will preferably comprise a compression spring placed around or adjacent the rod and adapted to urge the sleeve or the element in a direction away from the first valve means.

The inventive valve arrangement is also able to provide a rapid function in which an originally set valve position for obtaining a final mixture or an intermediate mixture can be quickly changed to the benefit of a value corresponding to 100% of the first medium and 0% of the second medium, by displacing the rod-like element axially to seal the second valve means and to fully open the first valve means by allowing said element, with the exception of the sleeve, to be displaced axially against a spring force by an applied force, from an original end position or intermediate position so as to seal-off the second valve means and to fully open the first valve means, wherein the valve bodies of said valve means are returned to their earlier mentioned original positions by the spring force when the force applied thereon is removed.

Advantages

Those advantages that are characteristic of an inventive valve arrangement reside in the provision of conditions which will enable a compact construction comprising only few components to be obtained and which is able to accurately mix at least two media, particularly gaseous media, and which is particularly adapted for use as a valve arrangement for mixing together air and oxygen gas in a pulmonary respirator, or as a valve for mixing anaesthetic gas and oxygen gas in an anaesthetic apparatus.

The primary characteristic features of an inventive valve arrangement are set forth in the characterising clause of the accompanying claim 1.

BRIEF DESCRIPTION OF THE DRAWINGS

A number of embodiments of different valve arrangements at present proposed and each having characteristic features and properties significant of the present invention will now be described with reference to the accompanying drawings, in which.

DETAILED DESCRIPTION OF EMBODIMENTS AT PRESENT PREFERRED

Figure 1:
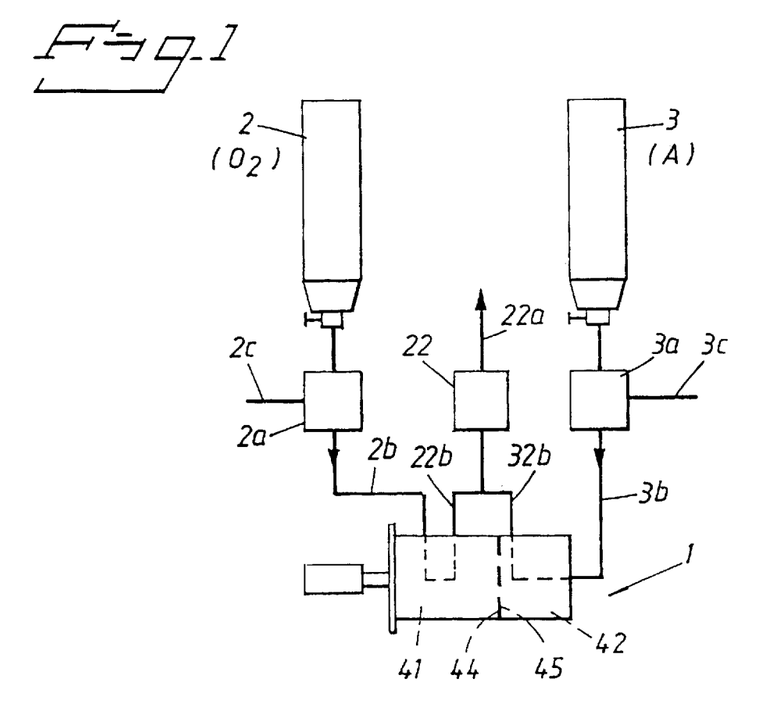
FIG. 1 illustrates schematically an inventive valve arrangement included as a part of a pulmonary respirator for obtaining an adapted and adjustable air-oxygen gas mixture.

Shown schematically in FIG. 1 is an inventive valve arrangement 1 that forms part of or is a component of a pulmonary respirator, or lung ventilator; said respirator not being shown for reasons of clarity.

Illustrated in FIG. 1 is a first container or gas bottle 2 which is completely or partially filled with oxygen gas ($O_2$), and a second container or gas bottle 3 which is completely or partially filled with compressed air (A).

The gas bottle 2 is connected to a pressure-regulating device 2a, and the gas bottle 3 is connected to a corresponding pressure regulating device 3a.

The gas pressure set by the device 2a is applied through a conduit 2b, whereas the gas pressure set by the device 3a is applied through a conduit 3b.

It lies within the scope of the invention to allow different pressures to prevail in the conduits 2b and 3b, resulting in a correspondingly different mixing ratio in a common mixing valve.

It is also possible with the aid of different embodiments of valve means used in the mixing valve to create conditions for different mixing ratios in response to different settings of the valve means.

In order to simplify the description of the inventive concept and with the intention of describing the embodiment most preferred, it is assumed in the following description that the same gas pressure prevails in the conduits 2b and 3b and that two similar valve means 10, 20 are used in mirror image with a central plane.

Thus, the gas pressures in the conduits 2b and 3b will normally be the same, wherewith the pressure in the conduit 2b and the pressure in the conduit 3b can be adjusted independently of each other through the medium of respective pressure regulating circuits 2c and 3b.

An increase in these pressures may result in a higher rate of flow, adapted for adult patients, through the mixing valve, while a decrease in said pressures may result in a lower rate of flow, adapted for children.

The embodiment illustrated in FIG. 1 is based on the assumption that the devices 2a and 3a are mutually identical and that the pressures prevailing in the conduits 2b and 3b are therewith also identical.

The rate of flow in the outgoing conduits 22b and 32b respectively can be adjusted through the medium of a needle valve 22 connected to a patient (not shown) by a tube or hose 22a.

The conduit 2b is connected to a first inlet of the valve arrangement 1, while the conduit 3b is connected to a second inlet of said valve arrangement.

The first inlet 10a of the valve arrangement 1 is connected to a first valve means 10, while the second inlet 20a of said valve arrangement is connected to a second valve means 20.

A first outlet 10b belongs to the first valve means 10, and a second outlet 20b belongs to the second valve means 20.

Each of the valve means 10 and 20 includes a cortical valve seat 10d and 20d respectively, and a respective conical valve body 10c and 20c, where the cone angle of the valve seats 10d, 20d is equal to the cone angle of the valve bodies 10c, 20c.

The cone angle-a-(FIG. 8) may conveniently be between 20 and 45°, particularly about 30° or slightly thereabove.

Figure 5:
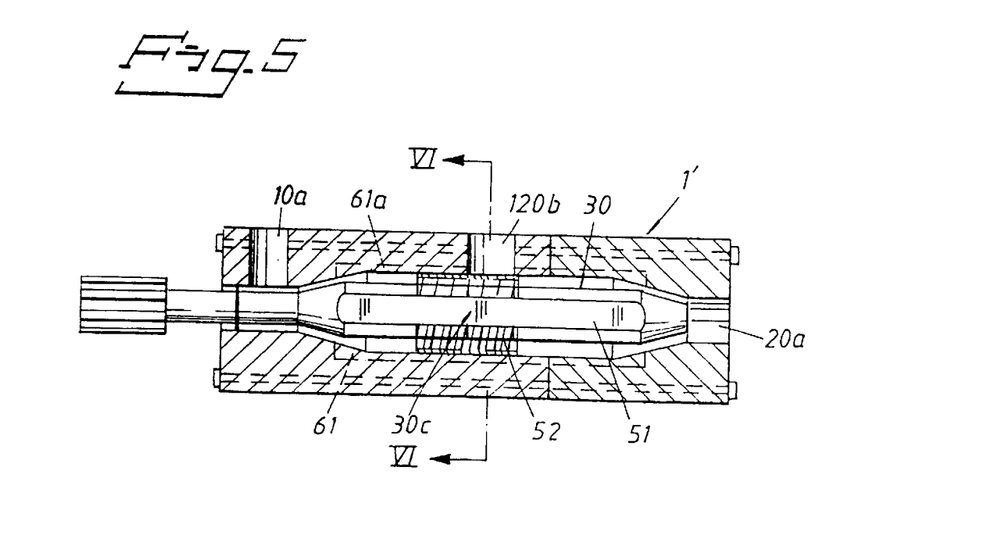
FIG. 5 is a sectioned side view of an alternative valve arrangement that has two inlets for two different gases, and a second outlet.
Figure 6:
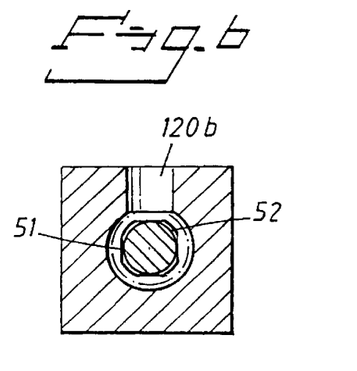
FIG. 6 is a central cross-sectional view of the arrangement shown in FIG. 5.
Figure 7:
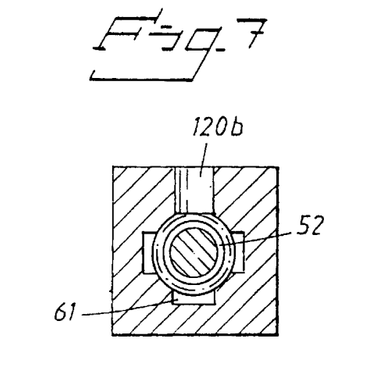
FIG. 7 is a central cross-sectional view of a further alternative embodiment of the arrangement shown in FIG. 5.

Referring back to FIGS. 1 and 2, it will be apparent therefrom that the valve arrangement 1 is particularly adapted for mixing together at least two media, such as air (A) and oxygen gas ($O_2$), and that the valve arrangement 1 includes said inlet 10a for a first valve means 10 adapted for a first medium ($O_2$), and said inlet 20a for a second valve means 20 adapted for a second medium (A), and an outlet 10b, 20b for respective media, or a single outlet for a mixture of said media obtained in the valve housing, this latter alternative being shown in FIGS. 5, 6 and 7.

Figure 2:
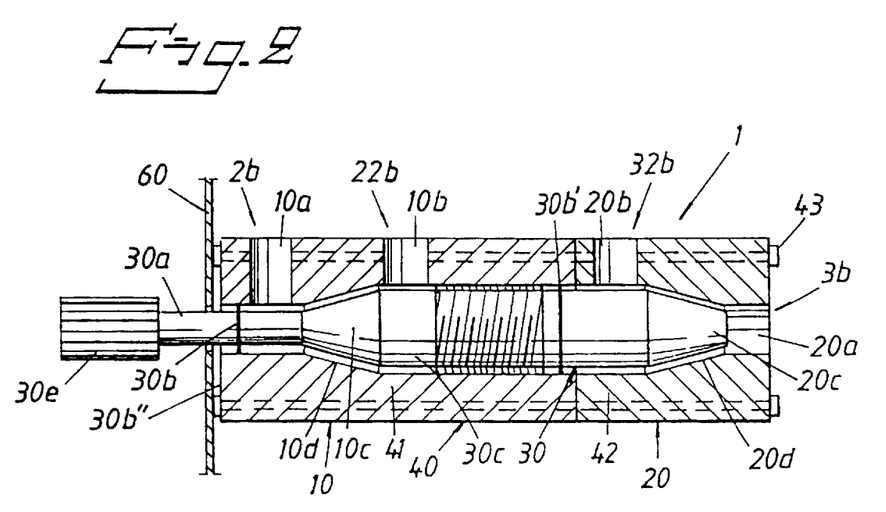
FIG. 2 is a longitudinal sectioned view of the valve arrangement according to FIG. 1 and shows two valve bodies in an intermediate position.

As will be seen particularly from FIG. 2, movement of the valve body 10c of the first valve means 10 away from and towards a first valve seat 10d, and movement of the valve body 20c of the second valve means 20 away from and towards a second valve seat 20d are mutually controlled so that an increase in the flow of the first medium through the first valve means 10 will result in a decrease in the flow of the second medium through the second valve means 20, and vice versa. Each selected mixture ratio shall result in the same total flow through the valve arrangement.

The first and second valve bodies 10c, 20c are formed on the end of a rod-like element 30.

The first valve seat 10d and the second valve seat 20d are formed as a part of a cavity 46 in a valve housing 40. The valve housing is divided at least into two parts and thus has a first part 41 and a second part 42 which are held together by known fastener means 43, said fastener means holding the housing parts 41 and 42 together by pressing cut surfaces 44, 45 sealingly together. The sealing means used to this effect is not shown.

Figure 4:
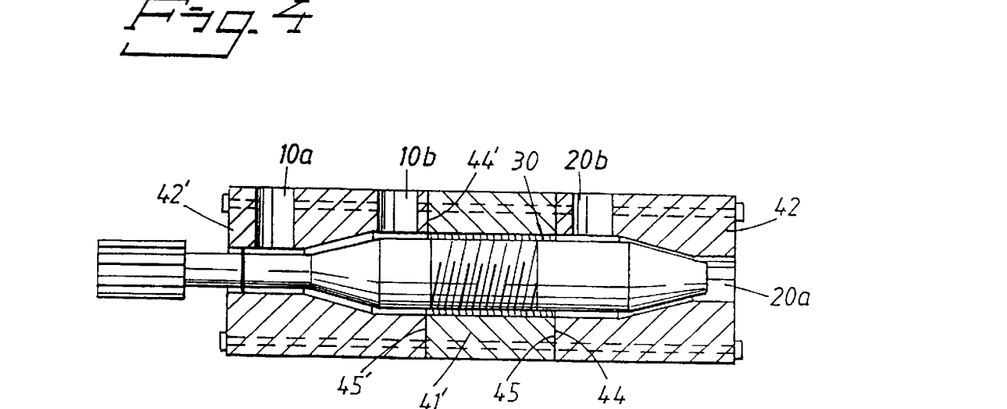
FIG. 4 shows the valve arrangement of FIG. 2 with one of the valve bodies in a first valve means located in a second end position.

The valve housing 40 may alternatively comprise three parts, two end parts 42, 42' and an intermediate part 41', where said end parts may be mutually identical with the exception of minor differences, namely with the exception of an inlet 10a (see FIG. 4).

The housing parts may be cylindrical in shape and include a threaded section for mutual coaction, or may be square shaped with a screw joint for mutual coaction, and have necessary seals.

Although the illustrated embodiment includes radially orientated cut surfaces 44, 45 and 44', 45' respectively, it will be understood that a chosen cut surface may be axially orientated.

Although the illustrated valve housing 40 is divided into two parts 41, 42 (according to FIG. 2), it will be understood that it lies within the scope of the invention to divide the valve housing into more parts than the three parts 41', 42, 42' illustrated in FIG. 4.

An inner cavity 46 of the valve housing 40 is comprised of a number of cavity sections, such as through-penetrating holes or openings 46a, 46b, said valve seats 10d and 20d, and an intermediate part 46c, wherein said intermediate part has a larger diameter than the holes 46a, 46b.

The intermediate part 46c is provided with a threaded portion or section 46c' and can be restricted to coaction with solely the housing part 41'.

The threaded part 46c' is in threaded coaction with the rod-like element 30, which also includes an intermediate part 30c having a thread 30c', which corresponds to the thread 46c'.

The rod-like element 30 has an end part 30e which is adapted to extend outside the valve housing 40 and adapted for rotation of the element 30.

As will be seen from FIG. 2, the rod-like element 30 is extended through an operating panel 60 in the form of a shaft 30a.

The valve housing 40 can be attached to the operating panel 60 by means of fasteners not shown. The rod-like element 30 is provided with gaskets or seals 30b and 30b', by inserting sealing rings into circular grooves provided on the peripheral surface of said element.

There is nothing to prevent the circular grooves accommodating said sealing rings from being placed in the cavity 46 of the valve housing.

In the embodiment illustrated in FIG. 2, the first valve seat 10d and the second valve seat 20d are conical in shape, with the widest part of the cones facing one another, and the first valve body 10c and the second valve body 20c are also conical in shape, with the widest part of the cones connecting with the externally threaded intermediate part 30c of the outer element 30c'.

Figure 3:
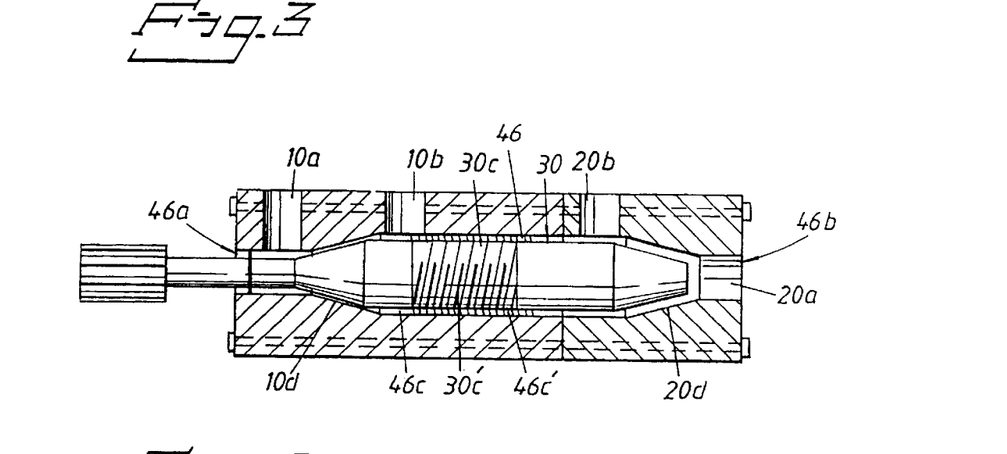
FIG. 3 shows the valve arrangement of FIG. 2 with one of the valve bodies in a first valve means located in a first end position.

In the illustrated case, the cones have an identical shape, so that the element 30 is able to be moved to a position fully to the left in FIG. 3 and therewith to seal-off communication between the inlet 10a and outlet 10b and create a fully open position between the inlet 20a and the inlet 20b.

As shown in FIG. 4, the rod-like element 30 can be moved fully to the right in said Figure, so that the inlet 20a will be completely closed against communication with the outlet 20b, while the inlet 10a, on the other hand, is fully open for coaction with the outlet 10b.

Mixture of the two gaseous media ($O_2$, A) takes place in each intermediate position between the end position shown in FIGS. 3 and 4, and when the same input pressure to the valve arrangement 1 for said media is selected, mixing of the media will take place under the same or essentially the same flow.

The threads 46c' and 30c' have mutually the same pitch which is adapted to move one of the valve bodies from a fully open position to a fully closed position against its valve seat, i.e. a displacement between the position shown in FIG. 3 and FIG. 4, in response to rotation of the element 30 through 1–6 turns, such as 2–4 turns.

With respect to the aforementioned seals, it can be mentioned that the seal 30b of the FIG. 2 embodiment is necessary whereas the seal 30b' may be omitted since the valve arrangement is concerned with mixing gaseous media and since it is not necessary for the seal between the threads 46c' and 30c' to be airtight.

However, the seal 30b' is necessary when the flow through solely the first valve means 10 or the flow through solely the second valve means 20 shall be measured.

Thus, it will be seen that a seal 30b is provided between the element 30 and the valve housing 40, adjacent one end-part of said housing (the left end in FIG. 2).

The seal 30b is disposed between said end-part of the element 30 and the valve housing 40 and seals the first medium or gas ($O_2$) in the subsection 46a of the cavity from passage to the surrounding space.

A seal 30b" is disposed between the operating panel 60 and the valve housing 40. Another seal may be placed between the operating panel 60 and the end-part 30a used to rotate the rod-like element.

These seals may conveniently consist of sealing rings placed in a circular groove.

Shown in FIGS. 5, 6 and 7 is an embodiment of a valve arrangement 1' that includes two inlets 10a, 20a, and an outlet 120b.

To this end, the rod-like element 30 has been provided with one or more axially orientated slots or planed surfaces 51. The illustrated case shows four mutually parallel slots or planed surfaces, which open into a circular groove 52 in the intermediate part 30c of said element, with the slots extending between the valve bodies 10c and 20c respectively.

These slots do not only extend between valve bodies but also slightly in over opposite valve bodies and therewith form appropriately dimensioned connecting paths for the two gaseous media to be mixed.

The valve housing 40 includes an outlet 120b, which connects with the groove 52.

FIG. 6 is a sectional view of the valve arrangement shown in FIG. 5.

An alternative embodiment is shown in FIG. 7 and in broken lines in FIG. 5. In this case, the valve housing 40 includes axially orientated slots, four slots in the illustrated case, where said slots co-act with a groove 52 in the intermediate part 30c of the element 30, or alternatively of the valve housing 40 provided with an outlet 120b positioned in connection with said groove.

Alternatively, the valve housing may be provided with at least one axially orientated slot 61a, which connects with the outlet 120b. This provides a large threaded area for the cavity 46 of the valve housing and a fully threaded area for the element 30.

Figure 8:
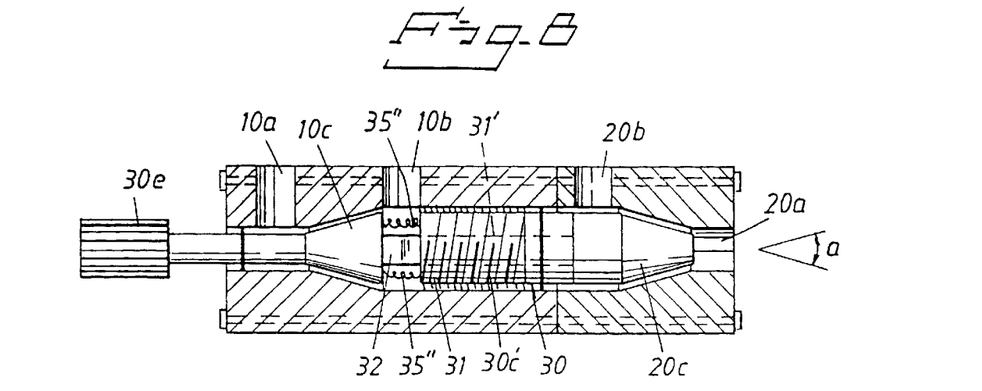
FIG. 8 is a sectioned side view of one embodiment of a valve arrangement that incorporates a rapid function which enables a set gaseous mixture to be altered to a setting in which only one gas is delivered, normally gaseous oxygen.

FIG. 8 shows an alternative valve arrangement in which the rod-like element 30 includes an intermediate sleeve 31 which is provided with an external thread 30c' and which is moveable axially in relation to the valve bodies 10c, 20c.

The valve bodies 10c, 20c are fixed in relation to each other via rod 32 and means for preventing relative rotation between the rod and the sleeve and/or impeding such rotation is provided between said rod and said sleeve.

Said means may be implemented by giving the rod a triangular or square cross-sectional shape or some corresponding shape that deviates from a circular cross-sectional shape, and by providing the sleeve with a central bore 31 whose cross-section corresponds to the cross-sectional shape of the rod.

Alternatively, said means may be provided by giving the rod 32' a circular cross-sectional shape and by giving the sleeve a central bore 31' of corresponding circular cross-sectional shape and by providing the rod and the sleeve with a keyway and a co-acting key 33.

This latter means may also be implemented by providing the rod 32 with a square cross-sectional shape and by providing the sleeve 31 with a bore 31' of corresponding shape.

The valve bodies 10c, 20c are fixed in relation to one another via said rod 32 and a means is provided between the rods 32 and the sleeve 31 for preventing their axial displacement.

Figure 9:
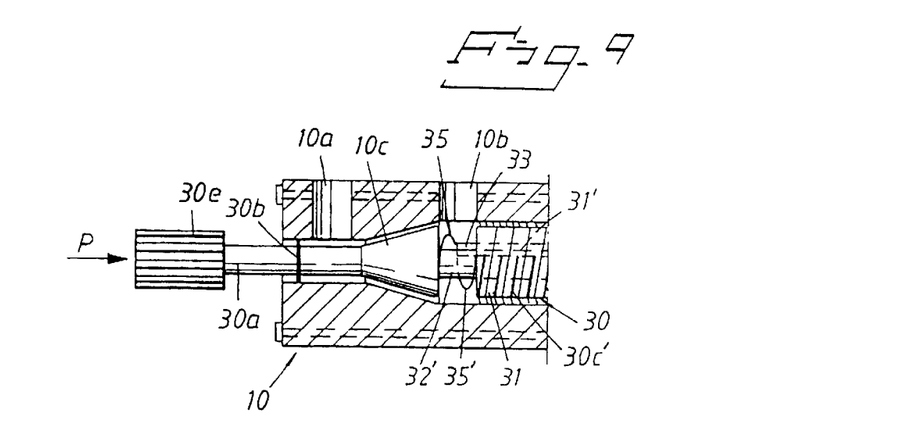
FIG. 9 is a sectioned side view of an alternative embodiment of the valve arrangement shown in FIG. 8.

One such means is shown in FIG. 9 and has the form of a spring unit 35. The spring unit 35 may be comprised of a compression spring 35' or of several compression springs 35".

One such spring unit 35' is shown placed around the rod 32' in FIG. 9. The spring is adapted to urge the sleeve 31 in a direction away from the first valve means 10 and its valve body 10c, and towards the second valve means 20 so as to rest against a support surface adjacent said second valve means.

The intention with the embodiment according to FIGS. 8 and 9 is to ensure that the air supply can be cut off completely and quickly when desired, via 20a and 20b, and to maximally increase the flow of oxygen gas, via 10a and 10b, to a maximum value (pure oxygen gas supply) without influencing the total flow through the valve arrangement 1 even when the valve arrangement is set for 0% oxygen gas and 100% air.

This is achieved by the fact that the rod-like element 30, except for the sleeve 31, can be displaced axially by an applied force P against a spring force 35' from one end position so as to close the valve means 10 completely or from an original intermediate position for sealing the second valve means 20 and a position in which the first valve means 10 is fully open.

When the force P acting on the element 30 is removed, the valve bodies of respective valve means 10, 20 will be returned to the aforesaid original positions by said spring force.

Figure 10:
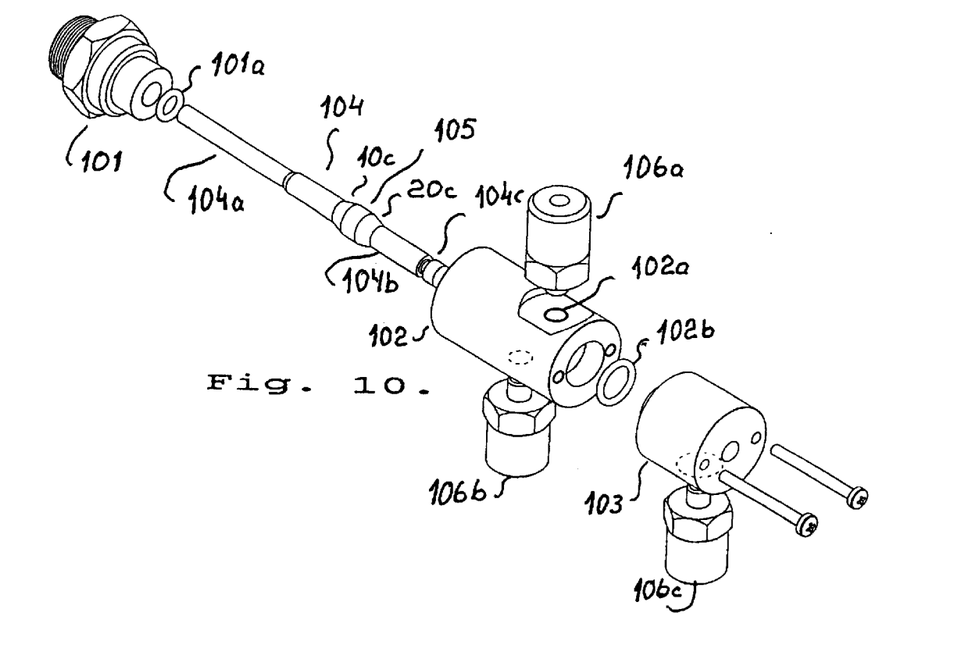
FIG. 10 is an exploded view of an embodiment with small outer dimensions.
Figure 11:
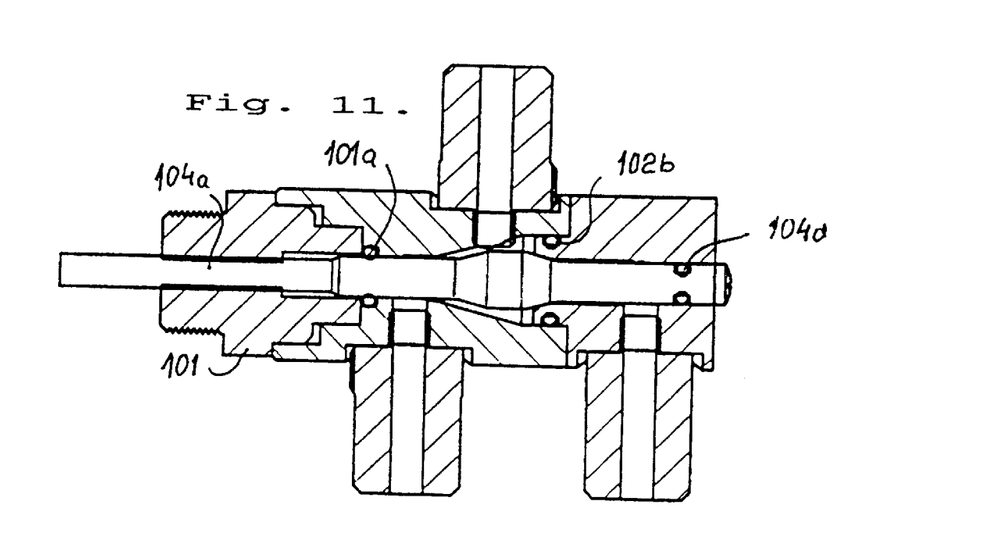
FIG. 11 is a cross-section of a valve arrangement according to FIG. 10.

In FIGS. 10 and 11 is shown a further alternative of an embodiment having the significant features related to the present invention. This embodiment forms the valve arrangement by using three parts 101, 102 and 103 and a rod-like element 104 having two valve bodies 10c and 20c and a very short intermediate section 105, intended to be oriented adjacent the outlet 102a and the adapter 106a.

Adapters 106a, 106b and 106c are identical and the adapter 106a is intended for the mixed gases.

The rod-like element 104 has a section 104a which exposes a threaded section adapted to co-operate with a threaded section inside part 101.

The rod-like element 104 has a section 104b, which is adapted for co-operation with a hole in part 103.

A grove 104c is intended to co-operate with a sealing ring 104d and another sealing ring 102b is arranged to cause a sealing between the parts 102 and 103.

A further sealing ring 101a is arranged to cause a sealing between the parts 101 and 102.

From FIG. 11 it is obvious that a turning of the threaded section 104a relatively to the part 101 and its threaded section causes the valve body 104 to move in one or the other direction and thus close one or the other valves.

Figure 12:
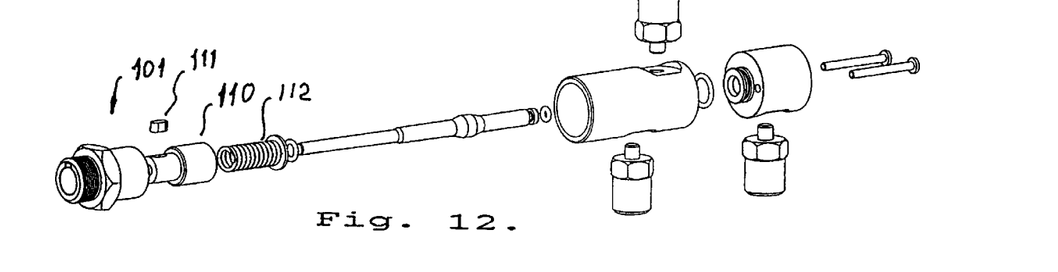
FIG. 12 is an exploded view of an embodiment with small outer dimensions but including a rapid function as illustrated in FIG. 8
Figure 13:
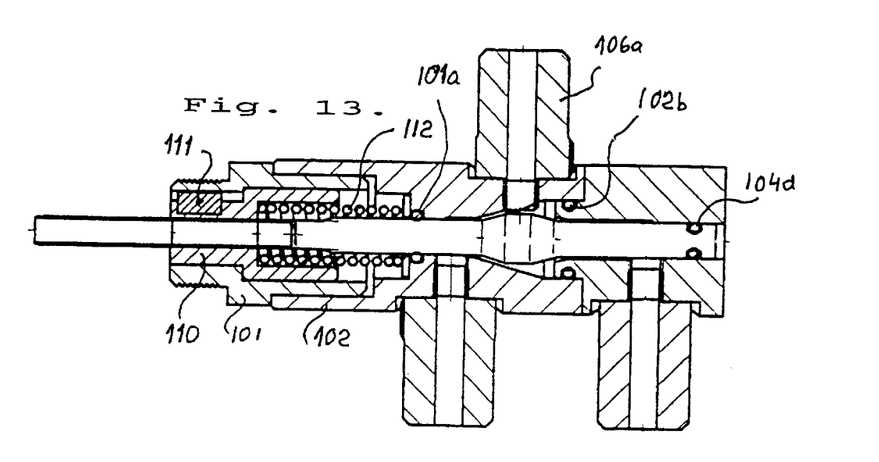
FIG. 13 is a cross-section of a valve arrangement according to FIG. 12.

FIGS. 12 and 13 show an embodiment with a rapid function as illustrated in FIG. 8. To this end part 101 is modified to include a sleeve 110 and a woodruff key or the like 111 and a spring arrangement 112. The reminding parts are the same as described in FIGS. 10 and 11 with a small modification to part 102.

It will be understood that the invention is not restricted to the afore described and illustrated exemplifying embodiments thereof and that modifications can be made within the scope of the inventive concept illustrated in the accompanying claims.

What is claimed is:

1. A valve arrangement adapted for mixing together at least two media, wherein said valve arrangement includes a first inlet and a first valve means for a first medium, and a second inlet and a second valve means for a second medium, wherein a movement of a valve body of a first valve means from and towards a first valve seat, and movement of the valve body of a second valve means from and towards a second valve seat are controlled mutually so that when a flow of said first medium through the first valve means increases the flow of the second medium through the second valve means will decrease, and vice versa, and wherein said first and second valve bodies are formed as a rod-like element, wherein said first valve seat and the second valve seat are formed in one and the same valve housing that comprises at least two parts; characterised in that an intermediate expanded part of said rod-like element and an inner expanded cavity in said housing are each provided with a threaded portion; in that said intermediate part of said rod-like element is provided with an external thread corresponding to said threaded portion; and in that one end-part of said rod-like element extends beyond said valve housing and is used for rotating said element.

2. A valve arrangement according to claim 1 and having two inlets and one outlet, characterised in that said element is provided with one or more axially orientated slots that open into a groove in the intermediate part; and in that the valve housing is provided with an outlet that connects with said groove.

3. A valve arrangement according to claim 1 and having two inlets and one outlet, characterised in that the valve housing is provided with one or more axially orientated slots; in that a groove is provided in the intermediate part of said element and/or in the cavity in said valve housing; and in that the valve housing is provided with an outlet that connects with said groove.

4. A valve arrangement according to claim 1 and having two inlets and one outlet, characterised in that the valve housing is provided with at least one axially orientated slot with said outlet connecting with said slot.

5. A valve arrangement according to claim 1, characterised in that said rod-like element has an intermediate externally threaded sleeve; and in that said sleeve can be displaced axially relative to said valve bodies.

6. A valve arrangement according to claim 5, characterised in that the valve bodies are fixed relative to each other via a rod; and is further characterised by means for preventing and/or impeding relative rotation of the rod and sleeve.

7. A valve arrangement according to claim 6, characterised in that said means is implemented by giving the rod a triangular or square or corresponding irregular cross-sectional shape, and by providing the sleeve with a hole whose cross-sectional shape conforms to the cross-sectional shape of said rod.

8. A valve arrangement according to claim 6, characterised in that said means is implemented by giving the rod a circular cross-sectional shape and by providing the sleeve with a central bore that has a corresponding circular shape, and by providing the rod and the sleeve with a keyway that co-acts with a key to this end.

9. A valve arrangement according to claim 5, characterised in that the valve bodies are fixed in relation to each other via a rod; and in that an axial displacement impeding means is provided between the rod and the sleeve.

10. A valve arrangement according to claim 9, characterised in that said means is comprised of a spring unit.

11. A valve arrangement according to claim 10, characterised in that said spring unit is comprised of one or more compression springs where one spring is placed around or adjacent said rod, and wherein said spring is adapted to urge the sleeve in a direction away from the first valve means.

12. A valve arrangement according to claim 9, characterised in that said element, except for the sleeve, is moveable axially in response to an applied force against a spring force from an original position in which the second valve means is fully closed and the first valve means is fully opened.

13. A valve arrangement according to claim 12, characterised in that the spring force functions to return the valve bodies of said valve means to an original position when said applied force is removed.

14. A valve arrangement adapted for mixing together at least two media, wherein said valve arrangement includes a first inlet and a first valve means for a first medium, and a second inlet and a second valve means for a second medium, wherein a movement of a valve body of a first valve means from and towards a first valve seat, and movement of the valve body of a second valve means from and towards a second valve seat are controlled mutually so that when a flow of said first medium through the first valve means increases the flow of the second medium through the second valve means will decrease, and vice versa, and wherein said first and second valve bodies are formed as a rod-like element, first valve seat and the second valve seat are formed in one and the same valve housing that comprises at least two parts; wherein an intermediate part or an end part of said rod-like element and an inner cavity in said housing are each provided with a threaded portion; wherein said intermediate part or end part of said rod-like element is provided with an external thread corresponding to said threaded portion; wherein one end-part of said rod-like element extends beyond said valve housing and is used for rotating said element, and wherein a seal arrangement is provided between said rod-like element and said cavity adjacent the threaded intermediate part.

15. A valve arrangement according to claim 14, characterised in that said seal comprises a sealing ring placed in a circular groove in said rod-like element.

16. A valve arrangement according to claim 1, characterised in that the valve housing is adapted to an operating panel with the end-part extending through and beyond the operating panel for a rotation of said rod-like element.

17. A valve arrangement according to claim 16, characterised by a seal disposed between the rod-like element and the valve housing, adjacent one end-part of said housing.

18. A valve arrangement according to claim 17, characterised in that said seal is disposed between the end-part of said rod-like element and the valve housing and functions to seal said first media from passage into a surrounding space.

19. A valve arrangement according to claim 17, characterised in that said seal is comprised of a sealing ring placed in a circular groove.

20. A valve arrangement according to claim 16, characterised by a seal disposed between the operating panel and the valve housing and/or the operating panel and the end-part used to rotate said rod-like element.

* * * * *

UNITED STATES PATENT AND TRADEMARK OFFICE
CERTIFICATE OF CORRECTION

PATENT NO. : 6,899,136 B1
DATED : May 31, 2005
INVENTOR(S) : Stefan Strömberg et al.

It is certified that error appears in the above-identified patent and that said Letters Patent is hereby corrected as shown below:

<u>Title page,</u>
Item [57], ABSTRACT, replace with the following:
-- A mixing valve (1) comprises a valve housing (40) that has an internal cavity (46) which forms two mutually opposing valve seats (10d, 20d). The cavity encloses an element (30) on which two valve bodies (10c, 20c) are formed. The cavity wall and the element have respective screw threads (46c', 30c') which enable two valve means (10, 20) to be actuated so as to open one of said valve means and close the other to passage of media therethrough. --.

Signed and Sealed this

Fourth Day of April, 2006

JON W. DUDAS
*Director of the United States Patent and Trademark Office*